United States Patent [19]

Matyas

[11] Patent Number: 5,776,106
[45] Date of Patent: Jul. 7, 1998

[54] REPLACEABLE FLEXIBLE PROTECTIVE COVER FOR AN INFUSION DEVICE

[76] Inventor: Melanie E. Matyas, 301 N. Duane Ave., San Gabriel, Calif. 91775

[21] Appl. No.: 368,097

[22] Filed: Jan. 3, 1995

[51] Int. Cl.$^6$ .................................................. A61M 5/32
[52] U.S. Cl. .................. 604/180; 604/174; 128/DIG. 26
[58] Field of Search .................................. 604/180, 174, 604/175, 93, 263; 128/DIG. 26

[56] References Cited

U.S. PATENT DOCUMENTS

| | | | |
|---|---|---|---|
| D. 302,041 | 7/1989 | Gentelia et al. | D24/52 |
| 3,782,378 | 1/1974 | Page | 128/133 |
| 3,900,026 | 8/1975 | Wagner | 128/133 |
| 4,519,793 | 5/1985 | Galindo | 604/180 |
| 4,633,863 | 1/1987 | Filips | 604/180 |
| 4,669,458 | 6/1987 | Abraham et al. | 128/133 |
| 4,898,587 | 2/1990 | Mera | 604/180 X |
| 4,976,698 | 12/1990 | Stokley | 604/174 |
| 5,074,847 | 12/1991 | Greenwell et al. | 604/180 X |
| 5,116,324 | 5/1992 | Brierley et al. | 604/180 |
| 5,336,204 | 8/1994 | Matyas | 604/263 |
| 5,520,629 | 5/1996 | Heinecke et al. | 604/180 X |

*Primary Examiner*—Sam Rimell
*Assistant Examiner*—Luke Yeh
*Attorney, Agent, or Firm*—Christie, Parker & Hale, LLP

[57] ABSTRACT

A replaceable flexible protective cover for an infusion device formed from a transparent membrane adhesive on one side affixable to the skin of a person to surround at least a part of the infusion device, and the membrane includes a portion through which a portion of the device passes and grips the infusion device to assure stability as well as added water proof characteristic to the cover.

12 Claims, 2 Drawing Sheets

REPLACEABLE FLEXIBLE PROTECTIVE COVER FOR AN INFUSION DEVICE

BACKGROUND OF THE INVENTION

1. Field of the Invention

This invention relates to a replaceable protective cover to cover an infusion device that is flexible and secured on a person to protect the device as well as waterproof it.

2. Description of the Prior Art

Applicant is of course familiar with her earlier U.S. Pat. No. 5,336,204 which is also directed to a protective cover for infusion devices. While the patent is certainly practical for protection due to its rigid body, it may have a slight disadvantage for proper adhesion on body contours due to its rigidity. In addition, the structure in the earlier patent was primarily for use to cover existing dressings that retain the catheter.

U.S. Pat. No. 3,900,026 employs a rigid body member. U.S. Pat. No. 3,782,378 requires a waist band to maintain an intravenous feeding tube where the tube passes under the shield which may allow moisture to penetrate beneath the shield. These are undesirable features.

SUMMARY OF THE INVENTION

One of the objects of the present invention is to provide a protective cover that is formed of soft pliable material that may easily seek the body contour and infusion devices where it is applied to seal the area and prevent moisture from entering the area to be protected.

Another object of the present invention is to provide a flexible protective cover that includes a plastic window that will allow visible inspection of the apparatus within the cover, such as a catheter or conventional Heparin lock.

A further object of the present invention is to provide a flexible protective cover that includes an opening therein to receive apparatus wherein it is waterproof and moisture cannot enter the protected area wherein a catheter is inserted.

A still further object of the present invention is to provide a flexible protective cover that includes a tab that contains a waterproof opening.

A yet further object of the present invention is to provide a flexible protective cover that includes a clear flexible plastic membrane to allow visual inspection and also can be stretched to conform to the apparatus inserted into the skin of a patient such as a Heparin lock.

Another object of the present invention is to provide a flexible protective cover that may include foam material such as cellular white foam of a cross linked polyurethane material.

A further object of the present invention is to provide a flexible protective cover that includes hypoallergenic adhesive to effect a waterproof adherence to the skin without skin irritation.

A still further object of the present invention is to provide a flexible protective cover capable of being mass produced in quantities by stamping out the same.

These and other objects and advantages will become apparent from the following part of the specification wherein details have been described for the competence of disclosure, without intending to limit the scope of the invention which is setforth in the appended claims.

BRIEF DESCRIPTION OF THE DRAWINGS

These advantages may be more clearly understood from the following detailed description and by reference to the drawing in which.

DETAILED DESCRIPTION OF THE PREFERRED EMBODIMENT

Figure 1:
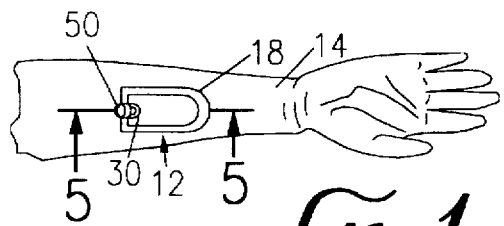
FIG. 1 is a top environmental view of the present invention in place upon the forearm of a patient.

A flexible protective cover generally designated 12 is seen as it is mounted on the forearm 14 of a person to protect infusion devices designated 16.

The flexible protective cover 12 is preferably elongated with an arcuate front end 18, a pair of spaced apart generally parallel side walls 20 and 22 and an end wall 24 joining the side walls 20 and 22. The cover, of the structure shown is a multilayer structure. In the embodiments shown in FIGS. 1 through 9 there is provided a middle layer 29 which is preferably fabricated from a cellular white foam of a cross linked polyurethane material. The middle layer 29 is is flexible and resilient and has a top surface 31 and a bottom surface 33. The middle layer 29 also has peripheral wall 35 having a predetermined geometrical shape. In the preferred embodiments of the present invention the preselected geometrical shape has an arcuate front wall portion 18, a pair of spaced apart substantially parallel side wall portions 20 and 22 and a back wall portion 24 spaced from the front wall portion 18. The front wall portion 18, the pair of side wall portions 20 and 22 and the back wall portion 24 define a central section 19 therebetween. The exact geometrical shape of the cover 12 defined by the peripheral wall 35 may be selected as desired for specific applications.

On the bottom surface 33 of middle layer 29 there is provided a flexible, resilient waterproof pressure sensitive adhesive layer 36 which, in preferred embodiments of the present invention is hypoallergenic so as to avoid skin irritations. The waterproof characteristic of the adhesive layer 36 insures that the moisture from regions external the cover 12 does not enter therethrough to the central section 19 so as to prevent or minimize the risk of infection from such moisture.

The adhesive layer 36 is substantially coextensive with the middle layer 29. The adhesive layer 36 has an inner surface 37 which is adhered to the bottom surface 33 of the middle layer 29 and the adhesive layer 36 has an outer surface 39 adapted to be adhered to the skin of the person using the cover 12.

A flexible, resilient waterproof top layer 42 is secured to the top surface 31 of the middle layer 29 by, for example, a suitable adhesive or by any other means. The top layer 42 is substantially coextensive with the middle layer 29 and the adhesive layer 36. The top layer 42 is a thin, transparent or at least clear layer of a tough plastic or other membrane suitable for the purpose.

The cover 12 has aperture walls 43 in the central section 19 which are spaced inwardly from the peripheral wall 35 to define a central aperture or cut out 26 extending through the middle layer 29 and the adhesive layer 36 and leaving a frame or rim section 51 of the middle layer 29 and the adhesive layer 36 between the aperture walls 43 and the peripheral wall 35. The portion of the adhesive layer 36 in the frame or rim section 51 is utilized to adhere the cover 12 to the skin of the person using the cover 12.

Tab walls 57 in the central section 19 define a mounting tab portion 30 which extends into the central section 19 from the aperture walls 43 which, in the embodiments shown in FIGS. 1 to 9 is adjacent the back wall portion 24. The mounting tab portion 30 has shank walls 59 defining a shank receiving aperture 61 which extends through the top layer 42, the middle layer 29 and the adhesive layer 36. The aperture 61 sealingly receives shank 54 of hub 50 of the infusion device 16 in a watertight sealing relationship to prevent moisture from entering therethrough to the interior of the central section 19. In some infusion devices such as a Heparin lock or hub there an annular grove 52 on the shank 54 and the shank receiving aperture 61 may be aligned with the annular grove 52 to provide the watertight seal with the shank 54.

In the embodiments of the present invention shown in FIGS. 1 to 8, the shank receiving aperture 61 is a hole 32. In the embodiments of the present invention shown in FIGS. 9 and 11 through 13 the shank receiving aperture 61 is a pair of crossed slits 32".

Figure 6:
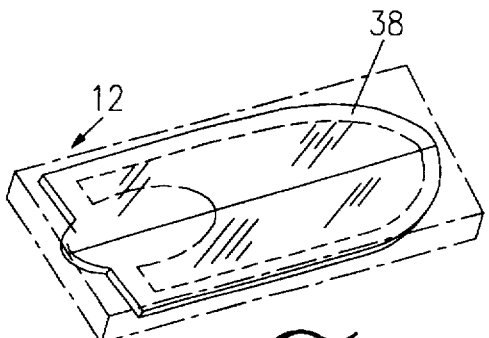
FIG. 6 is a bottom plan view of the present invention.

A removable adhesive protection layer 38 is on the outer surface 39 of the adhesive layer 36 and, as shown in FIG. 6 may extend continuously on the entire cover 12. The protection layer 38 may be paper, plastic or other suitable materials as is well known in the pressure sensitive adhesive layer art. The adhesive protection layer 38 is kept in place until the cover 12 is ready to be installed on the skin of the person using the cover 12. At other times the adhesive protection layer 38 protects the cover 12 from external contamination.

When it is desired to use the cover 12 the protection layer 38 is peeled off and the adhesive layer 36 is pressed on the skin of the person at the desired location.

The top layer 42 is preferably transparent or at least sufficiently clear so that the area of the skin underlying the central aperture or cut out 26 and the portions of the infusion device 16 such as the catheter needle 46 is visible for inspection purposes.

While the central aperture or cut out 26 is shown as conforming in geometrical shape to the geometrical shape of the peripheral walls 25, other geometrical shapes may be selected as desired for particular applications.

Figure 5:
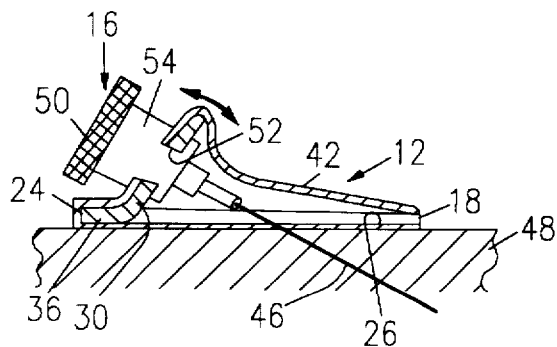
FIG. 5 is a cross sectional view of the invention taken on line 5—5 on FIG. 1.

The infusion device 16 includes a conventional catheter needle 46, see FIGS. 5, which is inserted into the skin 48 of a patient into a vein. The needle 46 may include a conventional Heparin lock hub 50 having a shank portion 54 so that a syringe (not shown) with an appropriate drug such as, for example, Heparin may be fitted to the lock hub 50 and the drug injected into the patient.

In the embodiments of the present invention utilized for Heparin infusion, and due to the fact that Heparin users do not have to have a constant continuous infusion of Heparin, a lock has been developed so that the catheter may be left in the arm and the dosage may be applied when required without the need to make new punctures in the skin 48.

With the relative permanency of the Heparin lock it is necessary to prevent moisture from entering the skin at the catheter and causing infection.

The present invention will accomplish the intended purpose. The plastic sheet or membrane 42 in the vicinity of the shank receiving aperture 61 such as hole 32 of tab 30 is, as noted above, cut to conform to the hole 32 or it may be cross cut as shown in the embodiments illustrated in FIGS. 9 and 11.

The diameter of the hole 32 is preferably slightly less that the diameter of the annular recess 52 of the shank 54 of the Heparin lock 50. The present invention may also be incorporated in a cover 12 for an infusion device 16 wherein the infusion device has a cylindrical shank and which does not include an annular groove such as annular groove 52 and still provide waterproof sealing relationship to such a cylindrical shank by appropriately sizing the aperture 61

Thus in practice the catheter needle 46 may be inserted into the skin 48 and the protective paper 38 of the cover 12 is then removed. The tab 30 of the cover 12 is bent upwardly, see FIG. 5, and the Lock hub 50 is inserted through the opening 32. The material of the cover 12 being resilient, the material around the opening 32 may be contorted and stretched so that a portion of the lock 50 may pass through the hole 32 and will seat on the shank 54 such as, for example, if present, the in the lock annular recess 52. With the hole 32 diameter being slightly smaller than the shank 54 such as, if present, recess 52 a good waterproof seal may be achieved.

Figure 2:
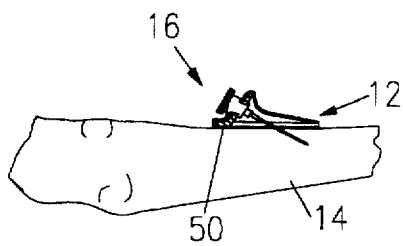
FIG. 2 is a side environmental view of the present invention in place upon the forearm of a patient.

As can be seen in FIGS. 1, 2 and 5 the hub 50 projects outward of the tab 30 so easy access is available for administering the required dosages at the times necessary yet leaving the infusion device free of moisture.

With the tab 30 elevated it will be noted that the clear plastic film being relatively tight on the cover device 12, it will adhere to the parts of the hub 50 thereunder, see FIG. 5. This will not only assure a greater water proofing, but will also act to stabilize the infusion device 16 while it is on a patient's body.

As the flexible cover 12 is secured to the skin 48 by means of the adhesive 36 and the seal around the shank 54 seals the interior, a complete water proof interior is available. In that way infusion devices 16 may be maintained on a patient's body for a longer period than usual as the chances of infection are reduced and the chances of the device being dislodged are reduced.

Figure 7:
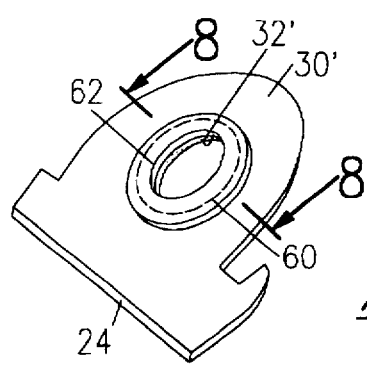
FIG. 7 is a prospective view of a protective cover with a modified waterproof opening.
Figure 8:
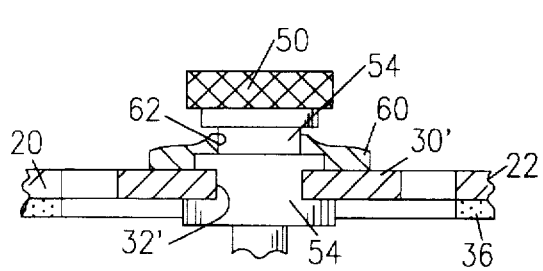
FIG. 8 is a view taken on lines 8—8 of FIG. 7.

The modified tab 30' as seen in FIGS. 7 and 8 includes a soft plastic annular donut seal 60 that may be secured on the tab 30' around the spark receiving aperture 61' such as the hole 32'. The annular opening 62 of the seal 60 is preferably slightly less that the diameter of shank 54 of the hub 50 so that when the hub 50 is inserted further water proofing is achievable.

Figure 9:
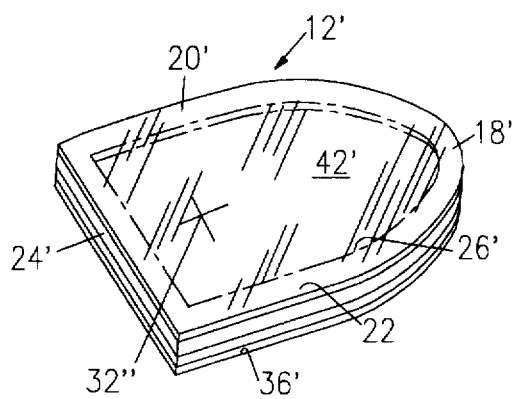
FIG. 9 is another modification of the protective cover.

In FIG. 9 there is illustrated a further modification of the protective cover 12'. Here the mounting tab 30 may be eliminated. However there is still a central aperture or cut out 26' defining a rim or frame formed by the space between the aperture walls 43' and the peripheral wall 25' having the arcuate front end 18', parallel side walls 20' and 22' and rear wall 24' forming a cut out 26'. The FIG. 9 structure still includes the adhesive 36' applied to the frame and the sheet plastic 42' applied as a top cover over all of the frame of the cover 12'.

The opening 32" for the Heparin lock 50 may be a cross cut as illustrated or an annular hole. In the case of this modification the lock 50 is mounted through the opening 32" and the sheet plastic 42' being flexible it will stretch around the infusion device 16, which in turn will help to water proof the device while surrounded by the protection device 12.

Figure 10:
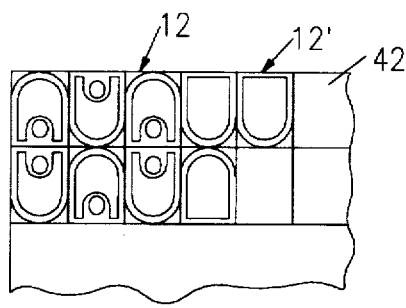
FIG. 10 is an illustration of how the protective cover may be fabricated from large sheets of material.

FIG. 10 illustrates a sheet of plastic 12 from which a quantity of the protective devices 12 may be formed.

Figure 11:
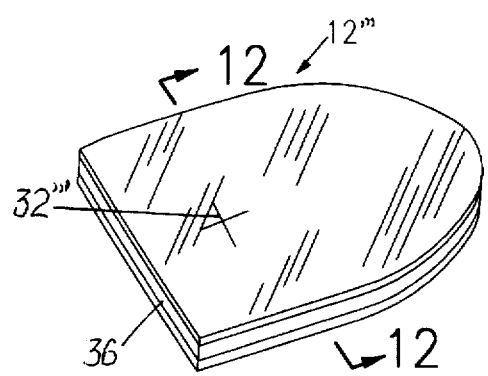
FIG. 11 is another modification of the protective cover.
Figure 12:
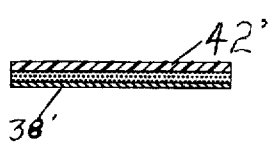
FIG. 12 is taken on line 12—12 of FIG. 11.
Figure 13:
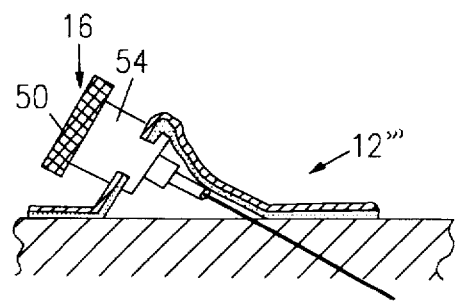
FIG. 13 is a side elevational view in section of the modification of FIG. 11.

FIGS. 11, 12 and 13 illustrate a second modification of the protective device 12'". This is a relatively simple but effective device that includes the plastic or membrane 42' in the shape shown or any other shape sufficient to cover the lock 50 (see FIG. 13).

The membrane 42' is coated on the underside with adhesive 36 that is preferably hypo-allergenic to avoid skin irritation. Placed to cover the adhesive 36 is a backing or cover 38' that may be peeled off so that the cover 12'" may be secured to the patient over lock 50. In addition there is preferably a cross cut 32'" that extends through the plastic 42', adhesive 36 and backing 38' to receive the lock 50.

One method of operation is for the hub or lock 50 to be inserted through the cross cut 32'" as seen in FIG. 13, then the backing 38' is removed and the infusion device inserted into the skin and the cover 12'" is secured to the skin and molded around the infusion device to assure a waterproof seal.

The invention and its attendant advantages will be understood from the foregoing description and it will be apparent that various changes may be made in the form, construction and arrangements of the parts without departing from the spirit and scope thereof or sacrificing its material advantages, the arrangements herein before described being merely by way of example. I do not wish to be restricted to the specific forms shown or uses mentioned, except as defined in the accompanying claims, wherein various portions have been separated for clarity of reading and not emphasis.

I claim:

1. A replaceable flexible protective cover for an infusion device, the infusion device having a shank portion defining an exterior hub portion and an interior portion having a catheter means insertable into the vein through the skin of a person, and the infusion device angled to the surface of the skin of the person for the condition of the catheter inserted into the skin of the person, the replaceable flexible protective cover comprising, in combination:

a flexible, resilient middle layer having a top surface and a bottom surface and a peripheral wall having a pre-determined geometrical configuration, and said peripheral wall having a front wall portion, a pair of spaced apart side wall portions and a back wall portion spaced from said front wall portion defining a central section therebetween;

a flexible, resilient, waterproof adhesive layer substantially coextensive with said middle layer and having an inner surface on said bottom surface of said middle layer and a outer surface, and said outer surface adapted to be adhered to the skin of the person;

a flexible, resilient waterproof top layer on said upper surface of said middle layer and substantially coextensive with said middle layer;

aperture walls in said central section defining a central aperture extending through said middle layer and said adhesive layer and said aperture walls spaced from said peripheral walls to define a frame section between said first walls and said peripheral wall;

shank walls in said central section and said shank walls defining a shank receiving aperture through said top layer, said middle layer and for receiving the shank of the infusion device in waterproof sealing relationship thereto.

2. The arrangement defined in claim 1 wherein:

said top layer is transparent, said adhesive layer is hypoallergenic and further comprising a removable cover layer on said outer surface of said adhesive layer for protecting said adhesive layer for the condition of said adhesive layer not affixed to the skin of the person.

3. The arrangement defined in claim 1 wherein: said shank receiving aperture comprises a hole.

4. The arrangement defined in claim 1 wherein: said shank receiving aperture is a pair of crossed slits.

5. The arrangement defined in claim 1 wherein: said middle layer is a cellular white foam layer of a cross linked polyurethane.

6. A replaceable flexible protective cover as defined in claim 1 wherein:

said frame section and said top layer is of a size adequate to surround and cover the skin of the person in said central aperture.

7. A replaceable flexible protective cover as defined in claim 6 wherein:

said frame section includes said arcuate front wall portion, said pair of spaced apart side wall portions and said back wall portion remote from said arcuate wall portion and extending between said side wall portions.

8. A replaceable flexible protective cover for an infusion device, the infusion device having a shank portion defining an exterior hub portion and an interior portion having a catheter means insertable into the vein through the skin of a person, and the infusion device angled to the surface of the skin of the person for the condition of the catheter inserted into the skin of the person, the replaceable flexible protective cover comprising, in combination:

a flexible, resilient middle layer having a top surface and a bottom surface and a peripheral wall having a pre-determined geometrical configuration, and said peripheral wall having a front wall portion, a pair of spaced apart side wall portions and a back wall portion spaced from said front wall portion defining a central section therebetween;

a flexible, resilient waterproof adhesive layer substantially coextensive with said middle layer and having an inner surface on said bottom surface of said middle layer and a outer surface, and said outer surface adapted to be adhered to the skin of the person;

a flexible, resilient waterproof top layer on said upper surface of said middle layer and substantially coextensive with said middle layer;

aperture walls in said central section defining a central aperture extending through said middle layer and said adhesive layer and said aperture walls spaced from said peripheral walls to define a frame section between said aperture walls and said peripheral wall;

tab walls in said central section and said tab walls defining a mounting tab portion and said mounting tab portion extending into said central section from a preselected position of said aperture wall, and said tab portion having shank walls defining a shank receiving aperture through said top layer, said middle layer and said adhesive layer for receiving the shank of the infusion device in waterproof sealing relationship thereto.

9. The arrangement defined in claim 8 wherein: said middle layer is a layer of cellular white cross linked polyurethane foam.

10. The arrangement defined in claim 8 wherein: said shank walls is a hole.

11. The arrangement defined in claim 8 and further comprising:

an annular donut seal means around said tab walls for providing said watertight sealing relationship to the shank of the infusion device.

12. The arrangement defined in claim 8 wherein: said mounting tab portion is bendable at said preselected portion of said aperture walls to be bent upwardly therealong, whereby the shank portion of the infusion device is mountable external said top layer and layer and sealed against moisture entering the interior of said central section from region external the top layer at said shank walls and the catheter needle is interior said central section and said interior of said central section is sealed from moisture entering the central section by said waterproof adhesive.

* * * * *

UNITED STATES PATENT AND TRADEMARK OFFICE
CERTIFICATE OF CORRECTION

PATENT NO. : 5,776,106

DATED : July 7, 1998

INVENTOR(S) : Melanie E. Matyas

Figure 4:
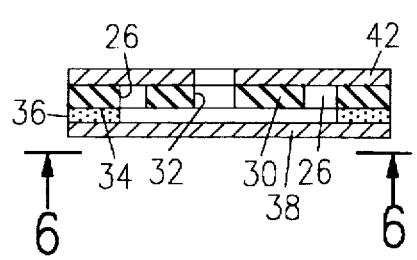
FIG. 4 is a cross sectional view of the present invention taken on lines 4—4 of FIG. 3.

It is certified that error appears in the above-identified patent and that said Letters Patent is hereby corrected as shown below:

The title page, showing the illustrative figs. 4 & 5 should be deleted and replaced with the attached title page, showing the illustrative figs. 4 & 5

UNITED STATES PATENT AND TRADEMARK OFFICE
CERTIFICATE OF CORRECTION

PATENT NO. : 5,776,106
DATED : July 7, 1998
INVENTOR(S) : Melanie E. Matyas

It is certified that error appears in the above-identified patent and that said Letters Patent is hereby corrected as shown below:

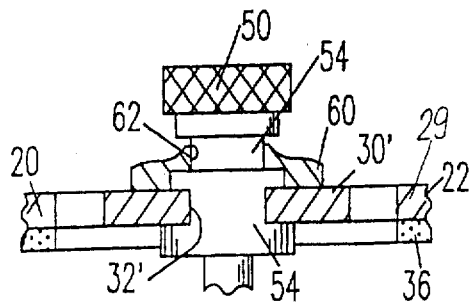

fig. 8

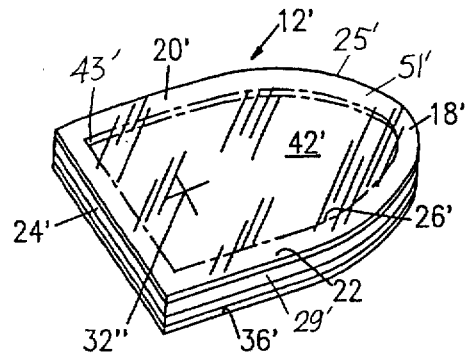

fig. 9

UNITED STATES PATENT AND TRADEMARK OFFICE
CERTIFICATE OF CORRECTION

PATENT NO. : 5,776,106
DATED : July 7, 1998
INVENTOR(S) : Melanie E. Matyas

It is certified that error appears in the above-identified patent and that said Letters Patent is hereby corrected as shown below:

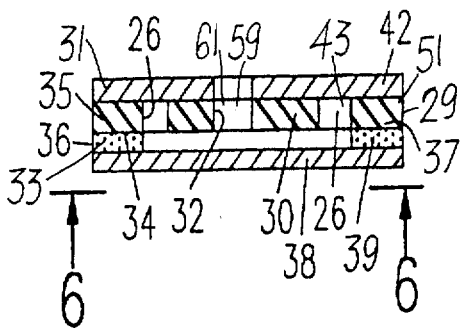

fig. 4

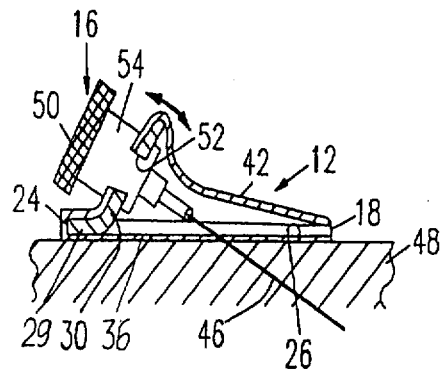

fig. 5

UNITED STATES PATENT AND TRADEMARK OFFICE
CERTIFICATE OF CORRECTION

PATENT NO. : 5,776,106
DATED : July 7, 1998
INVENTOR(S) : Melanie E. Matyas

It is certified that error appears in the above-identified patent and that said Letters Patent is hereby corrected as shown below:

In the Drawings, Sheets 1 and 2, replace FIGS. 1, 3, 4, 5, 8, and 9 as follows:

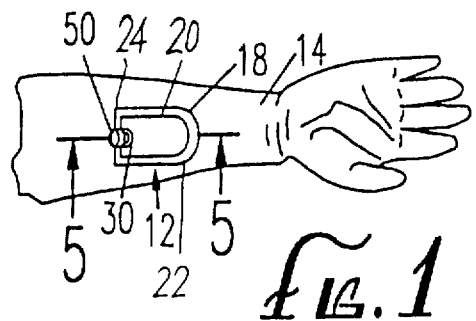

fig.1

Figure 3:
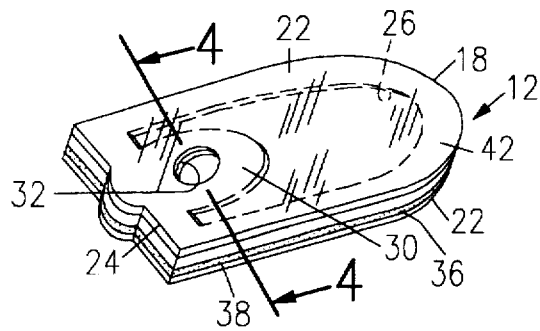
FIG. 3 is a prospective view of a protective cover of the present invention.

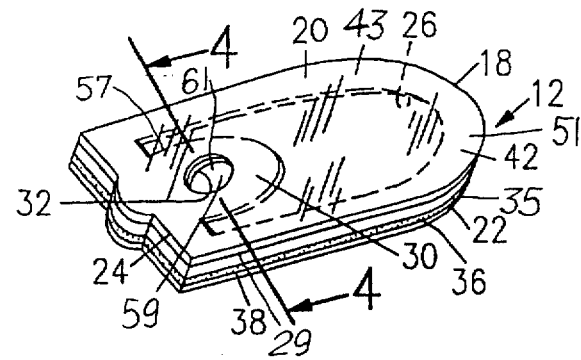

fig.3

UNITED STATES PATENT AND TRADEMARK OFFICE
CERTIFICATE OF CORRECTION

PATENT NO. : 5,776,106
DATED : July 7, 1998
INVENTOR(S) : Melanie E. Matyas

It is certified that error appears in the above-identified patent and that said Letters Patent is hereby corrected as shown below:

Column 1, line 62, replace "setforth" with -- set forth --.
Column 2, line 34, after "The cover" delete the comma.
Column 2, line 38, replace "layer 29 is is" with -- layer 29 is --.
Column 3, line 26, replace "there an annular grove" with
　　-- there is an annular groove --.
Column 3, line 28, replace "grove" with -- groove --.
Column 3, line 59, replace "FIGS. 5" with -- FIG. 5 --.
Column 4, line 13, replace "less that" with -- less than --.
Column 4, line 20, after "aperture 61" insert a period.
Column 4, line 24, replace "Lock" with -- lock --.
Column 4, line 29, replace "the in the lock" with -- the lock in the --.
Column 4, line 55, replace "less that" with -- less than --.
Column 5, line 58, replace "a outer" with -- an outer --.
Column 6, line 47, replace "a outer" with -- an outer --.
Column 7, line 2, after "shank" insert -- receiving aperture defined by
　　said shank --.
Column 8, line 3, after "top layer" delete "and layer".

Signed and Sealed this

Thirtieth Day of November, 1999

Attest:

Q. TODD DICKINSON

Attesting Officer　　Acting Commissioner of Patents and Trademarks